United States Patent [19]
Teronen et al.

[11] Patent Number: 5,652,227
[45] Date of Patent: Jul. 29, 1997

[54] INHIBITION OF THE DEGRADATION OF CONNECTIVE TISSUE MATRIX PROTEIN COMPONENTS IN MAMMALS

[76] Inventors: Olli Pekka Teronen, Kylänvanhimmankuja 9B, FIN 00640, Helsinki; Timo Arto Sorsa, Hakolahdentie 37 A 1, FIN 00200 Helsinki; Tuula Anneli Salo, Rantakoskelantie 5 B 9, FIN 90570 Oulu, all of Finland

[21] Appl. No.: 380,581

[22] Filed: Jan. 30, 1995

[51] Int. Cl.$^6$ .................................................. A61K 31/66
[52] U.S. Cl. ............................................................ 514/75
[58] Field of Search ................................................ 514/75

[56] References Cited

U.S. PATENT DOCUMENTS

| | | |
|---|---|---|
| 4,234,645 | 11/1980 | Gunther et al. . |
| 5,157,027 | 10/1992 | Biller et al. . |

FOREIGN PATENT DOCUMENTS

| | | |
|---|---|---|
| 0088462 | 9/1983 | European Pat. Off. . |
| 0054997 | 3/1986 | European Pat. Off. . |
| 2813121 | 10/1978 | Germany . |
| 1588284 | 4/1981 | United Kingdom . |
| WO8909775 | 10/1989 | WIPO . |
| WO9015806 | 12/1990 | WIPO . |
| WO9421266 | 9/1994 | WIPO . |
| WO9423770 | 10/1994 | WIPO . |
| WO9426279 | 11/1994 | WIPO . |

OTHER PUBLICATIONS

Teronen et al., *Characterization of Interstitial Collagenases in in Jaw Cyst Wall*, Scandinavian Journal of Dental Research, vol. 3, pp. 1–19 (1995).

Suomalainen, *Interstitial Collagenases in Gingival Crevicular Fluid and Saliva in Periodontal Diseases*, University of Helsinki, Finland, 1993.

Teronen et al, *Identification and Characterization of Gelatinases/Type IV Collagenases in Jaw Cysts*, Journal of Oral Pathology & Medicine, vol. 23, pp. 1–7, 1994.

Ingman et al, *Multiple Forms of Gelatinases/Type IV Collagenases in Saliva and Gingival Crevicular Fluid of Periodontitis Patients*, Journal of Clinical Periodontology, vol. 26, pp. 26–31, 1994.

Ingman et al, *Collagenase, Gelatinase and Elastase Activities in Sulcular Fluid of Osseointegrated Implants and Natural Teeth*, Journal of Clinical Periodontology, vol. 21, pp. 301–307, 1994.

Fleisch, *Biophosphonates Pharmacology and Use in the Treatment of Tumour–Induced Hypercalcaemic and Metastatic Bone Disease*, Drugs, vol. 42, No. 6, pp. 919–944, 1991.

Lauhio et al, *In vivo Inhibition of Human Neutrophil Collagenase (MMP–8) Activity During Long–Term Combination Therapy of Doxycycline and Non–Steroidal Anti–Inflammatory Drugs (NSAID) in Acute Reactive Arthritis*, Clin Exp Immunol, vol. 98, pp. 21–28, 1994.

Santavirta et al, *Role of Mesenchymal Collagenase in the Loosening of Total Hip Prosthesis*, Clinical Orthopaedics and Related Research, vol. 290, pp. 206–214, May 1993.

Sorsa et al, *Partial Purification and Characterization of Latent Human Leukocyte Collagenase*, Medical Biology, vol. 63, pp. 66–72, 1985.

Konttinen et al, *Substrate Specificity and Activation Mechanisms of Collagenase from Human Rheumatoid Synovium*, Matrix, vol. 11, pp. 395–403, 1991.

Suomalainen et al, *Specificity of the Anticollagenase Action of Tetracyclines: Relevance to Their Anti–Inflammatory Potential*, Antimicrobial Agents and Chemotherapy, vol. 36, No. 1, pp. 227–229, Jan. 1992.

Sorsa et al, *Collagenase in Synovitis of Rheumatoid Arthritis*, Seminars in Arthritis and Rheumatism, vol. 22, No. 1, pp. 44–53, Aug. 1992.

Birkedal-Hansen, *Role of Matrix Metalloproteinases in Human Periodontal Diseases*, J Periodontol, vol. 64, No. 5, pp. 474–484, May 1993.

Kowolik et al, *The Effect of Dichloromethylene Bisphosphonate on Human Gingival Crevicular Neutrophil Myeloperoxidase Activity*, Archs Oral Biol, vol. 35, pp. 201S–203S, 1990.

Vincenti et al, *Using Inhibitors of Metalloproteinases to Treat Arthritis*, Arthritis & Rheumatism, vol. 37, No. 8, pp. 1115–1126, Aug. 1994.

Birkedal–Hansen et al, *Matrix Metalloproteinases: A Review*, Critical Reviews in Oral Biology and Medicine, vol. 4, No. 2, pp. 197–250, 1993.

Felix et al, *The Effect of Several Diphosphonates on Acid Phosphohydrolases and Other Lysosomal Enzymes*, Biochimica et Biophysica Acta, pp. 429–438, 1976.

Fleisch, *Bisphosphonates in Bone Disease*, Stampfli & Co., Ltd., Graphic Enterprise, Bern, 1993.

Greenwald, *Guidelines For Clinical Trial Design for Evaluation of MMP Inhibitors*, Annals New York Academy of Sciences, pp. 273–279, (1994).

DE Clerck et al., *Matrix Metalloproteinases and Their Inhibitors in Tumor Progression*, Annals New York Academy of Sciences pp. 222–232, (1994).

Krane, *Clinical Importance of Metalloproteinases and Their Inhibitors*, Annals New York Academy of Sciences, pp. 1–21 (1994).

Sorsa et al., *Effects of Tetracyclines on Neutrophil, Gingival, and Salivary Collagenases*, Annals New York Academy of Sciences, pp. 112–131 (1994).

Primary Examiner—James J. Seidleck
Assistant Examiner—John M. Cooney, Jr.
Attorney, Agent, or Firm—Browdy and Neimark

[57] ABSTRACT

Bis-phosphonates such as clodronate, etidronate, pamidronate and alendronate are found to inhibit the degradation of connective tissue matrix protein components in mammals, including humans, and therefore are useful in the therapeutic and prophylactic treatment of mammals against a variety of physiological and pathological connective tissue disorders or extracellular protein degradation disorders including wounds, burns, fractures, lesions, ulcers, cancer and metastasis progression in connective tissues, rheumatoid arthritis and other arthitides, periodontitis, peri-implantitis, cysts, root canal treatment, AIDS, ulceration of the cornea, gastric ulceration, aftae, trauma, acne, psoriasis, loosening of end-osseal hip-protheses.

17 Claims, 5 Drawing Sheets

INHIBITION OF THE DEGRADATION OF CONNECTIVE TISSUE MATRIX PROTEIN COMPONENTS IN MAMMALS

FIELD OF INVENTION

The present invention relates to treatments for reducing degradation of connective tissue matrix protein components, and more particularly to the use of bis-phosphonates in the treatment or prophylaxis of connective tissue degradation disorders or extracellular protein degradation disorders in mammals, especially humans.

BACKGROUND OF THE INVENTION

Matrix metalloproteinases (MMPs) constitute a family of genetically related proteolytic enzymes which are capable of cleaving almost all protein constituents of the extracellular matrix. MMPs take part in the extracellular matrix destruction and remodeling in both physiological and pathological conditions, e.g. in wound healing, cancer and metastasis progression, rheumatoid arthritis, periodontitis, etc. (Krane, S. M., Ann. N.Y. Acad. Sci. 732:1–10, 1994, Woessner, J. F. Jr., Ann. N.Y. Acad. Sci. 732:11–21, 1994).

Nine MMPs have been disclosed so far in the literature: fibroblast-type collagenase (MMP-1), 72K gelatinase (MMP-2), stromelysin-1 (MMP-3), putative metalloproteinase-1 (MMP-7), PMN-type collagenase (MMP-8), 92K gelatinase (MMP-9), stromelysin-2 (MMP-10), stromelysin-3 (MMP-11) and macrophage metalloelastase. Each of the MMP enzymes contains a putative tridentate $Zn^{2+}$-binding site which is believed to constitute the active site in the enzyme (Birkedal-Hansen, H., J. Periodontol. 64:474–484, 1993).

A comprehensive review of the MMPs, their known modes of action, their inhibition by various compounds as well as details of the involvement of MMPs in various pathological conditions and diseases is given in the above mentioned Ann. N.Y. Acad. Sci. 732 and also by Birkedal-Hansen et al. in Crit. Rev. Oral Biol. Med. 4:197–250, 1993, the relevant disclosures of which are incorporated herein by reference.

MMPs and/or their endogenous inhibitors are frequently found in cells, tissue and interstitial fluids, and it is believed that they play an important role in the remodeling of the extracellular matrix. They are associated with rapid cell movements and in the reshaping of the extracellular matrix during growth. Increased amounts of MMPs are expressed also during the invasive growth of primary tumors and metastases, and they seem also to induce expression of MMPs in adjacent stromal cells (DeClerck, Y. A. et al., Ann. N.Y. Acad. Sci. 732:222–231). A link is believed to exist between destruction of joints in rheumatoid arthritis and the expression and action of MMPs and proteolytic cascades related to them (Sorsa, T. et al., Semin. Arth. Rheum. 22:44–53, 1992). Also loosening of hip-prostheses has been shown to involve the expression and action of MMPs, especially MMP-1 (Santavirta et al., Clin. Orthoped. Res. 290:206–215, 1993). MMP-8 seems to be predominant in gingiva, gingival crevicular fluid and saliva in periodontal diseases (Sorsa et al., Ann. N.Y. Acad. Sci. 732:112–131, 1994) and peri-implant sulcular fluid (Ingman et al., J. Clin. Periodontol. 21:301–307, 1994).

There is a variety of other disorders in which extracellular protein degradation plays a prominent role. Examples of such diseases include arthritides, acquired immune deficiency syndrome (AIDS), burns, wounds such as bed sores and varicose ulcers, fractures, trauma, gastric ulceration, skin diseases such as acne and psoriasis, lichenoid lesions, epidermolysis bollosa, aftae (reactive oral ulcer), dental diseases such as periodontal diseases, peri-implantitis, cysts and root canal treatment or endodontic treatment related diseases, etc.

Although MMPs are believed to play a major role in the degradation of interconnective tissues and their components, so far there is little evidence of the specific role and mechanism of the separate enzymes in the biological environment. Since the actual mechanism of the MMPs is not known, finding inhibitors for the various MMPs is based more on experimental testing than on theoretical considerations.

A number of synthetic and natural inhibitors for MMPs have been found and tested for a possible usefulness as described by Vincenti et al. in Arth. Rheum. 37:1115–1126, 1994. Thus, chelating agents and moieties including EDTA, hydroxamate, thiol, phosphonamidate, phosphinate and phosphoramidate groups have been tested (Birkedal-Hansen et al. Crit. Rev. Oral Biol. Med. 4:197–250, 1993). Various sulfur-based inhibitors have also been tested but no very good results have been obtained (Vincenti et al. Arth. Rheum. 37:1115–1126, 1994). Tetracyclines have been found to inhibit MMPs, especially MMP-8 although the inhibition mechanism is not known (Golub et al., Curr. Op. Dent. 2:80–87, 1992; Suomalainen et al., Antimicrobial, Agents & Chemother. 36:227–229, 1992; Sorsa et al., Ann. N.Y. Acad. Sci. 732:112–131, 1994; Lauhio et al., Clin. Exp. Immunol. 98:21–28, 1994)

As disclosed for instance in the above mentioned Ann. N.Y. Acad. Sci. 732, it is envisaged that specific inhibitors could be produced by polyclonal and monoclonal antibodies to various MMP-enzymes. α-Macroglobulins are also known to inactivate susceptible proteinases and may function as MMP inhibitors. Tissue inhibitors of metalloproteinases (TIMPs) are known to inhibit the activity of the active forms of MMPs.

Although the above discussion shows that inhibitors for MMPs do exist and have been investigated, the tests are still mostly at the experimentation stage and no clinically acceptable inhibitor for MMPs exists as a therapeutic or prophylactic drug for any of the pathological states and diseases potentially connected with MMPs. Adverse side effects, which have been detected in the above described MMP inhibitors include, for instance, toxicities (synthetic peptides), antimicrobial activities (tetracyclines), etc.

While the MMP-dependent reactions provide the mechanism for at least one of the key pathways by which the structural macromolecules of interstitial connective tissues are degraded, it is to be observed that mineralized matrices are believed to be degraded by a totally different reaction mechanism. This is the osteoclastic pathway which is based, at least in part, on a release of acidic thiol proteinases to a specific area on the mineralized matrix surface.

Bisphosphonates constitute a group of compounds known to have an effect on the mineralized matrices of the body. Bisphosphonates are compounds characterized by a P-C-P bond. Several bisphosphonates have been investigated in humans and animals with respect to their effect on bone and bone derived cells. They are especially known for their ability to inhibit bone resorption (Fleisch, H., Drugs 42:919–944, 1991).

No effect of bisphosphonates on other tissues than bone has been reported. Despite the fact that bisphosphonates have been studied on human neutrophil myeloperoxidase (Kawolick et al., Arch. Oral Biol. 35:2015–2035, 1990), on enzymes capable of producing reactive oxygen species and on non-specific hydroxylases and acidic serine proteinases (Felix et al., *Biochem. Biophys. Arch.* 429:429–438, 1979), no effects of bisphosphonates on collagenase, gelatinase or other MMP activities have been noted. In a round table discussion reported in said *Ann. N.Y. Acad. Sci.* 732: 273–279, 1994, bisphosphonates are mentioned only in connection with bone resorption and osteoclasts. The effects of bisphosphonates on matrix metalloproteinases participating in connective tissue protein matrix destruction has until now been unknown.

SUMMARY OF THE INVENTION

The present inventors have now surprisingly found that bisphosphonates have a marked inhibitive effect on matrix metalloproteinases (MMPs) and that they consequently are capable of inhibiting the degradation of connective tissue matrix protein components in mammals.

It is therefore an object of the present invention to provide a method useful in the treatment of connective tissue degradation disorders by inhibiting the activity of MMPs in a mammalian system.

The present invention relates to a method for reducing a pathologically excessive degradation of connective tissue matrix protein components in mammals, e.g. humans, by administering to said mammal a bisphosphonate the presence of which is effective in reducing the matrix metalloproteinase (MMP) activity in said mammal. More particularly the method comprises administering to the mammal an effective amount of bisphosphonate which results in a significant reduction of the MMP dependent protein degradation in said mammal.

The present invention also relates to pharmaceutical preparations of a wide variety, which preparations include an amount of bisphosphonate effective to reduce the activity of one or more MMPs.

The present invention also includes the use of bisphosphonates for the preparation of a composition to be administered to mammals in the treatment or prophylaxis of connective tissue degradation disorders or extracellular protein degradation disorders.

The bisphosphonates which are useful in the method of the present invention include bisphosphonates which are active as inhibitors against matrix metalloproteinases (MMPs), especially against one or both of the following MMPs: MMP-1 and MMP-8, both of which have a significant impact on the protein degradation system in mammals in inflammatory and other diseases (Krane, *Ann. N.Y. Acad. Sci.* 732: 1–10, 1994).

Examples of suitable bisphosphonates include commercially available bisphosphonates such as clodronate, etidronate, pamidronate, tiludronate, etc. An especially preferred bisphosphonate for use in the present invention is clodronate which has been shown to inhibit the activity of MMP-1 and MMP-8.

The amount of bisphosphonate to be used in the method of the present invention varies depending on the specific bisphosphonate used, the patient to be treated as well as on the route of administration. According to the invention it is even possible to use, without substantial changes, the various bisphosphonates in the dosage forms which are commercially available for the treatment of bone disorders. Thus, the present invention provides the practitioner instantly with a new way of treating patients suffering from connective tissue matrix protein degradation while using a drug which is known to be safe, non-toxic and well tolerated.

As a result of the present invention, mammals suffering from an excessive matrix metalloproteinase activity in the connective tissue system may now be treated to prevent or reduce matrix protein degradation. Mammals with diseases such as ulceration of the cornea, cancer invasion and metastasis, AIDS, rheumatoid arthritis, gastric ulceration, burns, wounds such as bed sores and varicose ulcers, fractures, trauma, gastric ulceration, skin diseases such as acne and psoriasis, lichenoid lesions, epidermolysis bollosa, aftae (reactive oral ulcer), dental diseases such as periodontal disease, periodontitis, peri-implantitis and root canal treatment (endodontic treatment) related disorders, loosening of end osseal hip-protheses, and other diseases and disorders which have extracellular matrix protein degradation as a part of the disease process, may be treated either with bisphosphonates alone or in combination with other drugs normally used in connection with the disease or disorder in question.

The present anti-collagenase therapy by bisphosphonates provides a valuable supplementary aid for the use by a medical, dental and veterinary practitioner in the control and treatment of, among others, such diseases as those mentioned above.

For better understanding of the present invention, together with other and further objects and the nature and advantages of the present invention, reference is made to the following detailed description of specific embodiments.

DETAILED DESCRIPTION OF THE INVENTION

In accordance with the present invention, a method for treating mammals suffering from excessive matrix protein component degradation in the connective tissue system is disclosed. The method comprises administering to the mammal an amount of a bisphosphonate that results in a significant reduction of said protein degradation.

The bisphosphonates useful in carrying out the method of the present invention are so called geminal bisphosphonates having the general formula In the bisphosphonates which have so far been studied, the substituents R' and R" independently stand for a hydrogen or a halogen atom, a hydroxy, optionally substituted amino or optionally substituted thio group or an optionally substituted hydrocarbon residue; preferably one of R' and R" is hydroxy, hydrogen or Cl. Other substituents which provide effective bisphosphonates are not intended to be excluded from the present invention.

Said geminal bisphosphonates are generally called merely bisphosphonates and it should be understood that a reference in the present disclosure to bisphosphonates is to be understood as referring to geminal bisphosphonates.

Several bisphosphonates have already been investigated on mammals. Thus, the bisphosphonates useful in practicing the present invention may be selected from the commercially available bisphosphonates used in humans, which include (1-hydroxyethylidene)bis-phosphonate (etidronate), (dichloromethylene)bis-phosphonate (clodronate), (3-amino-1-hydroxypropylidene)bis-phosphonate (pamidronate), and (4-amino-1-hydroxybutylidene)bis-phosphonate (alendronate).

Other bisphosphonates useful in carrying out the present method further include the following bisphosphonates investigated for their effect on bone in humans: {[4-chlorophenyl)thio]methylene}bis-phosphonate (tiludronate), (6-amino-1-hydroxyhexylidene)bis-phosphonate, [1-hydroxy-2-(3-pyridinyl)-ethylidene]bis-phosphonate (risedronate), [3-(dimethylamino)-1-hydroxypropylidene]bis-phosphonate, [1-hydroxy-3-(methylpentylamino)propylidene]bis-phosphonate (BM 21.0955).

There are also a number of bisphosphonates which have been used in animals and these are also contemplated as being useful in the present invention, e.g. [(cycloheptylamino)methylene]bis-phosphonate (YM 175), [1-hydroxy-3-(1-pyrrolidinyl)-propylidene]bis-phosphanate (EB-1053), [1-hydroxy-2-(1H-imidazol-1-yl) ethylidene] bis-phosphonate (CGP 42'446), and (1-hydroxy-2-imidazo-[1,2-a]pyridin-3-yl-ethylidene) bis-phosphonate (YM 529). The bisphosphonates useful in carrying out the present invention are, however, not intended to be limited to the above mentioned compounds.

A comprehensive study of known bisphosphonates is given by Fleisch, H., *Drugs* 42(6):919–944, 1991, the disclosure of which is incorporated herein by reference.

Bisphosphonates are commercially available for clinical applications focused on four areas. They are used as (a) skeletal markers in the form of $^{99m}$technetium derivatives for diagnostic purposes in nuclear medicine; (b) antiosteolytic agents in patients with increased bone destruction, especially Paget's disease, tumor bone disease and, recently, osteoporosis; (c) inhibitors of calcification in patients with ectopic calcification and ossification; (d) antitartar agents added to toothpastes.

The bisphosphonates used or investigated for use in bone disease have, in general the following properties: they bind strongly onto bone mineral, inhibit calcium phosphate crystal formation and dissolution, inhibit normal and ectopic mineralization (suggested mechanism being physicochemical inhibition of crystal growth), and inhibit bone resorption. The exact mechanism in bone resorption has not been elucidated.

The toxicity of bisphosphonates is in general low and they are well tolerated. The relatively few adverse effects of bisphosphonates include gastrointestinal intolerability, especially with some amino derivatives and inhibition of normal mineralization. One significant negative side effect of bisphosphonates, especially etidronate, in prolonged administration is generally related to their activity on bone, i.e. they not only stop the resorption of bone, which is a desired effect as anti-osteolytic agent, but they may also prevent mineralization entirely, and this is the reason that especially etidronate is normally administered only for a short term followed by a delay of three months.

The amount of bisphosphonate administered to reduce mammalian matrix protein degradation in the connective tissue system according to the present invention is an amount that significantly reduces MMP activity. In the preferred embodiment of the present invention, the bisphosphonate is administered in an amount sufficient to significantly reduce the activity of the collagenases MMP-1 and MMP-8.

It is obvious that the dosages of the various bisphosphonate analogs will vary somewhat from each other and the ranges set forth below are only illustrative and should not be taken as limiting the range of doses. The person skilled in the art will be able to determine an optimal dosage of the selected bisphosphonate on the basis of his or her experience.

For illustrative purposes, a suitable amount of the preferred bisphosphonate, clodronate, is about 100 to 5000, and even up to 10,000 mg/kg/day in oral therapy and 0.1 to 10 mg/kg/day in infusion, such as at 2.5 mg/kg/day i.v. for a week or up to 6400 mg/kg/day p.o. for 5–300 days. The preferred method of treatment includes clodronate compositions administered in suitable pharmaceutical carriers or devices.

Etidronate may be used at the usual dosage amounts of from 5 mg/kg/day p.o. or i.v. for three days up to 400 mg/kg p.o. for six months, preferably for only 3–14 days and then repeated after three months. Pamidronate may be administered at the usual dosage of 1 mg/kg i.v. for 24 hours to 1200 mg/kg/day p.o. for six days or 300 mg/kg/day p.o. for 13 months. Alendronate and BM 21.0955 are reported to be effective in the treatment of calcemia at a single dose of 10 mg and 2–4 mg, respectively, and can be so used in the present invention, although preferably for a longer term of at least two weeks.

The pharmaceutical dosage forms may be in the form of capsules, tablets, solutions or suspensions suitable for oral administration of the bisphosphonate to the affected mammal. The bisphosphonates may also be intravenously administered in the form of infusions in suitable solvents such as a saline solution, or as injectable solutions. In some situations a topical treatment is preferred and the pharmaceutical composition may be formed into creams, pastes, gums, jellies, ointments, liquids, drops, aerosols, plasters, membranes, etc.

The pharmaceutical preparation according to the present invention may also incorporate the bisphosphonate in a polymeric carrier delivery system for topical or local delivery to the afflicted area.

A topical administration is especially suitable for treating locally affected areas of the mammal such as the gingiva in the case of periodontitis, peri-implantitis or root canal treatment, the cornea in the case of an ulceration of the cornea, the lungs in the case of lung cancer, the skin in the case of acne or psoriasis or skin diseases involving tissue destruction such as bed sores, varicose ulcers, etc.

Specific dental preparations include mouth rinse or mouth wash liquids, tooth pastes, dental floss, guided tissue regeneration (GTR) membranes, chewing gums, periodontal or surgical pastes, laquers, etc. Especially in the case of periodontal diseases it may be preferable to incorporate the bisphosphonate into a polymeric carrier which may be delivered therein directly to the afflicted area. The periodontal pockets may also be topically treated with bisphosphonate preparations by various techniques either at home by home care devices or at the dentist by chair-side devices such as ultrasonic systems.

While bis-phosphonates have been added to toothpaste as indicated above for removing tartar already formed on the teeth, bis-phosphonates have never been proposed for the treatment of periodontal disease. Diabetes patients are especially prone to suffer from periodontitis but are not known to suffer from osteoporosis any more than the general public. Dental preparations according to the present invention are therefore particularly suitable for the treatment of periodontitis and the prophylactic treatment of periodontitis in diabetes patients.

Eye drops will be suitable for application to the eyes. Aerosols or sprays may be used for damaged lungs caused by burns, wounds or cancer and for preventing metastases. The person skilled in the art will be able to select the form of preparation which is best suited for the disease or disorder in question.

For prophylactic administration, the patients should preferably be selected from at-risk populations, such as diabetics and health care workers.

The following Examples illustrate the invention without, however, limiting it in any way.

EXAMPLE 1

Inhibition of Purified Human Fibroblast collagenase (MMP-1) by clodronate

Purified trypsin-activated human fibroblast-type MMP-1 (Konttinen et al., Matrix, 11:395–403; for trypsin-activation of latent pro-MMPs, see Sorsa et al., Med. Biol. 63:66–72, 1985) was incubated with purified 1.5 µM type I collagen in different indicated clodronate concentrations and buffer for 20 hours at 22° C. Preincubations of MMP-1 with the buffer and clodronate before adding the substrate lasted 1 hour at 22° C. After addition of Laemmli's sample buffer, the samples were immediately heated to 100° C. for 5 minutes. Subsequently the reaction products were separated on sodium dodecyl sulfate polyacrylamide gel electroforesis (SDS-PAGE) (Sorsa et al., Med. Biol. 63:66–72, 1985) using 8–10% crosslinked gels. The gels were stained with Coomassie brilliant blue and the stain intensity of collagen α- and αA chains was quantified using LKB Ultroscan Densitometer model 2202 coupled with Axxiom chromatography computer program. The value representing the αA chains (the ¾ cleavage fragments) was multiplied by ⁴⁄₃ and its proportion of total collagen in the sample was measured. Four separate incubations were used to obtain the mean values and the standard deviations presented in FIG. 1.

Figure 1:
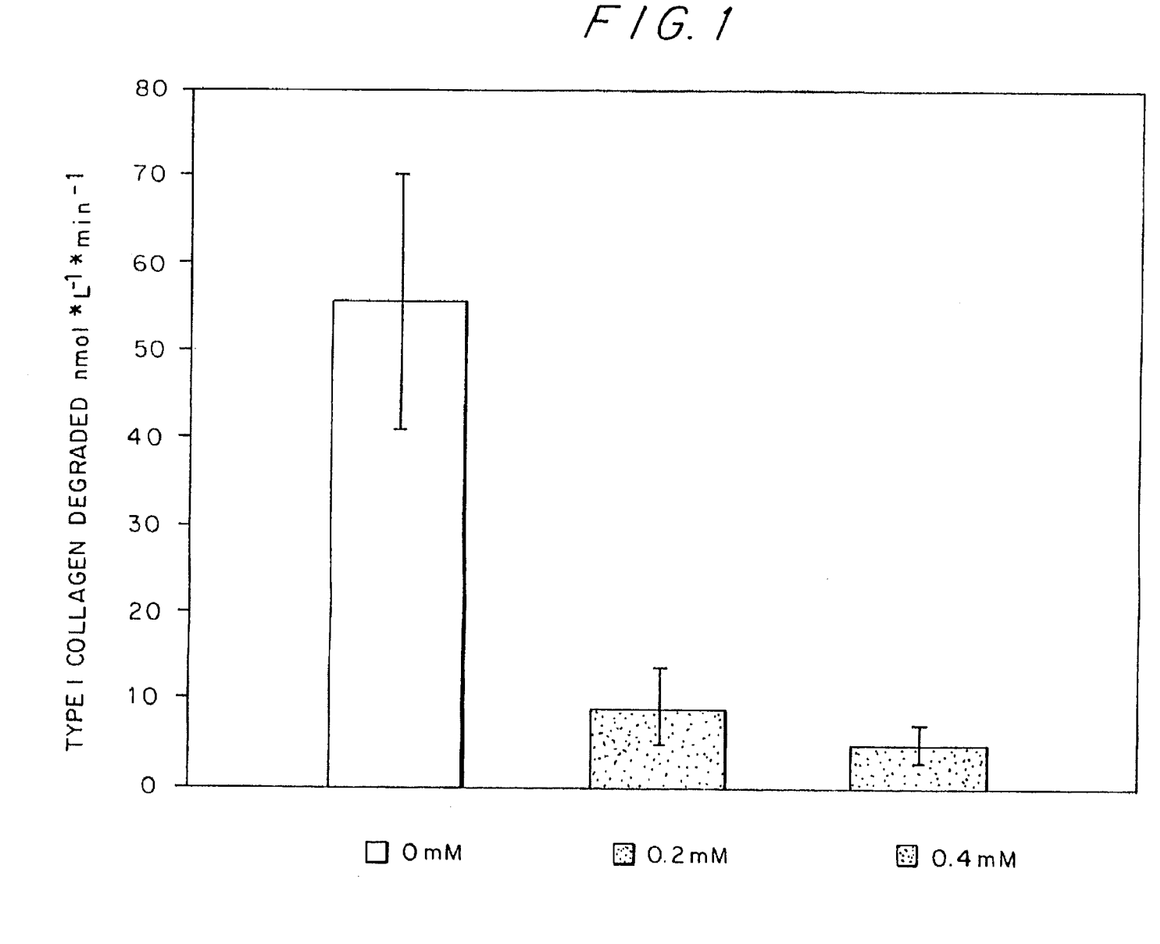
FIG. 1 is a block graph of the effects of clodronate on purified human fibroblast-type collagenase (MMP-1) activity.

FIG. 1 shows a diagram presenting the effect of clodronate on trypsin-activated purified MMP-1. The columns present mean values with standard deviations of four separate incubations. The concentrations of clodronate are indicated.

EXAMPLE 2

Inhibition of Collagenase Activity in Jaw Cyst Tissue Samples by Clodronate

Extracts from jaw cyst tissue containing collagenase activity were prepared according to the methods used previously by the inventors (Teronen et al., Eur. J. Oral. Sci., in press, 1994; Teronen et al., J. Oral. Pathol. Med., in press, 1994). The extracts were preincubated with the concentrations of clodronate indicated in FIG. 2, at 22° C. for 1 hour before addition of type I collagen and incubation for 60 hours at 22° C. The protocol for the measurement of collagenase activity was the same as in Example 1. The effects of clodronate at different concentrations on the collagenolytic activity present in the cyst extracts are presented in FIG. 2.

Figure 2:
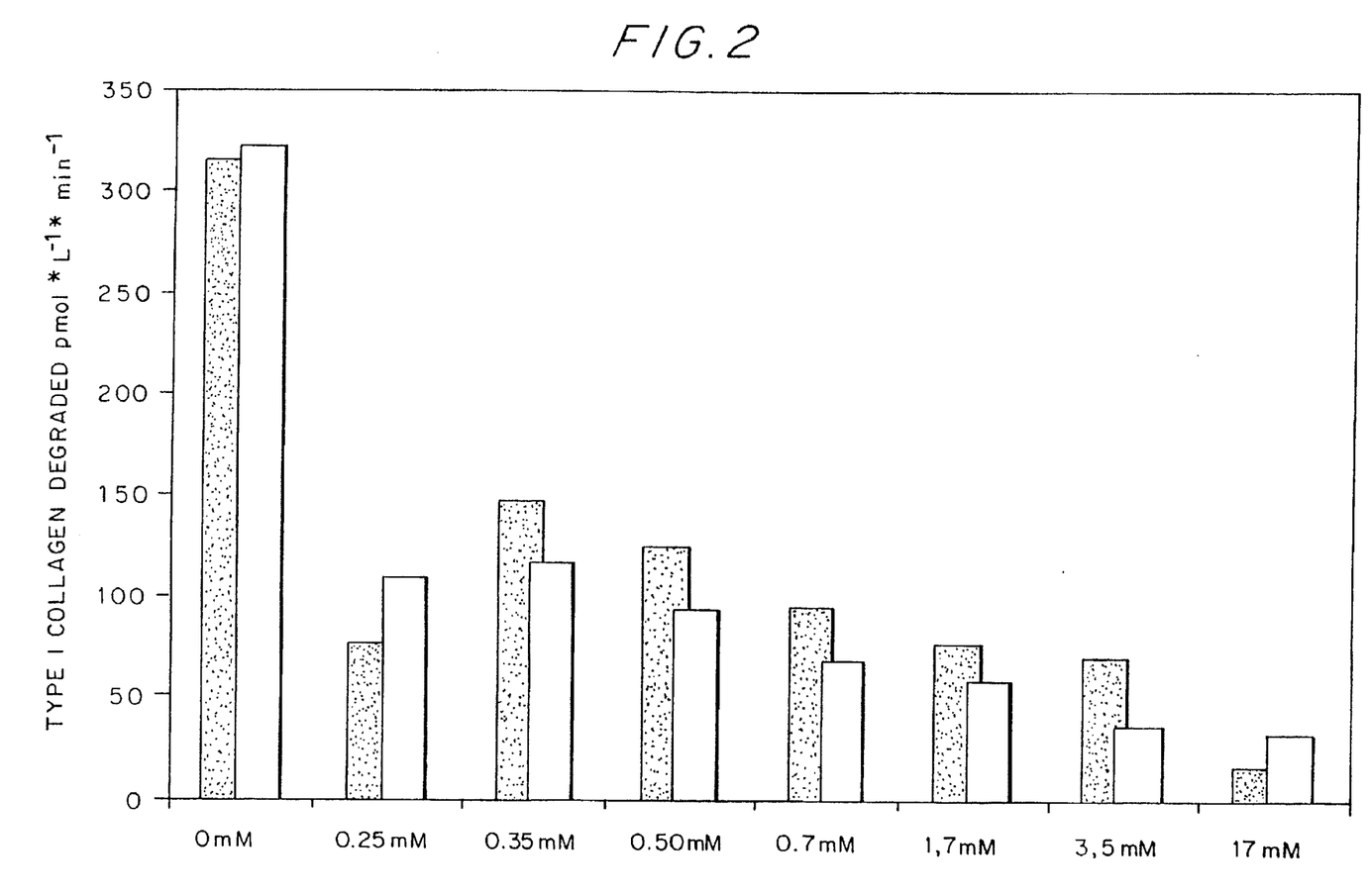
FIG. 2 is a block graph of the effects of clodronate on collagenase activity present in jaw cyst extracts.

FIG. 2 shows a diagram of the effect of clodronate on autoactive cyst collagenase activity at different concentrations presented below each column. Two series are shown.

EXAMPLE 3

Inhibition of Purified Human Neutrophil Collagenase (MMP-8) by Clodronate

Purified human MMP-8 activated by aminophenyl mercuric acetate (APMA) (Sorsa et al., Med. Biol. 63:66–72, 1985) was incubated with purified 1.5 µM type I collagen in different clodronate concentrations and buffer for 20 hours at 22° C. Preincubations of MMP-8 with the buffer and clodronate before adding the substrate lasted 1 hour at 22° C. After addition of Laemmli's sample buffer, the samples were immediately heated to 100° C. for 5 minutes. Subsequently the reaction products were separated on sodium dodecyl sulfate polyacrylamide gel electroforesis (SDS-PAGE) (Sorsa et al., Med. Biol. 63:66–72, 1985) using 8–10% crosslinked gels. The gels were stained with Coomassie brilliant blue and the stain intensity of collagen α- and αA chains was quantified using LKB Ultroscan Densitometer model 2202 coupled with Axxiom chromatography computer program. The value representing the αA chains (the ¾ cleavage fragments) was multiplied by ⁴⁄₃ and its proportion of total collagen in the sample was measured. Four separate incubations were used to obtain the mean values and the standard deviations presented in FIG. 3.

Figure 3:
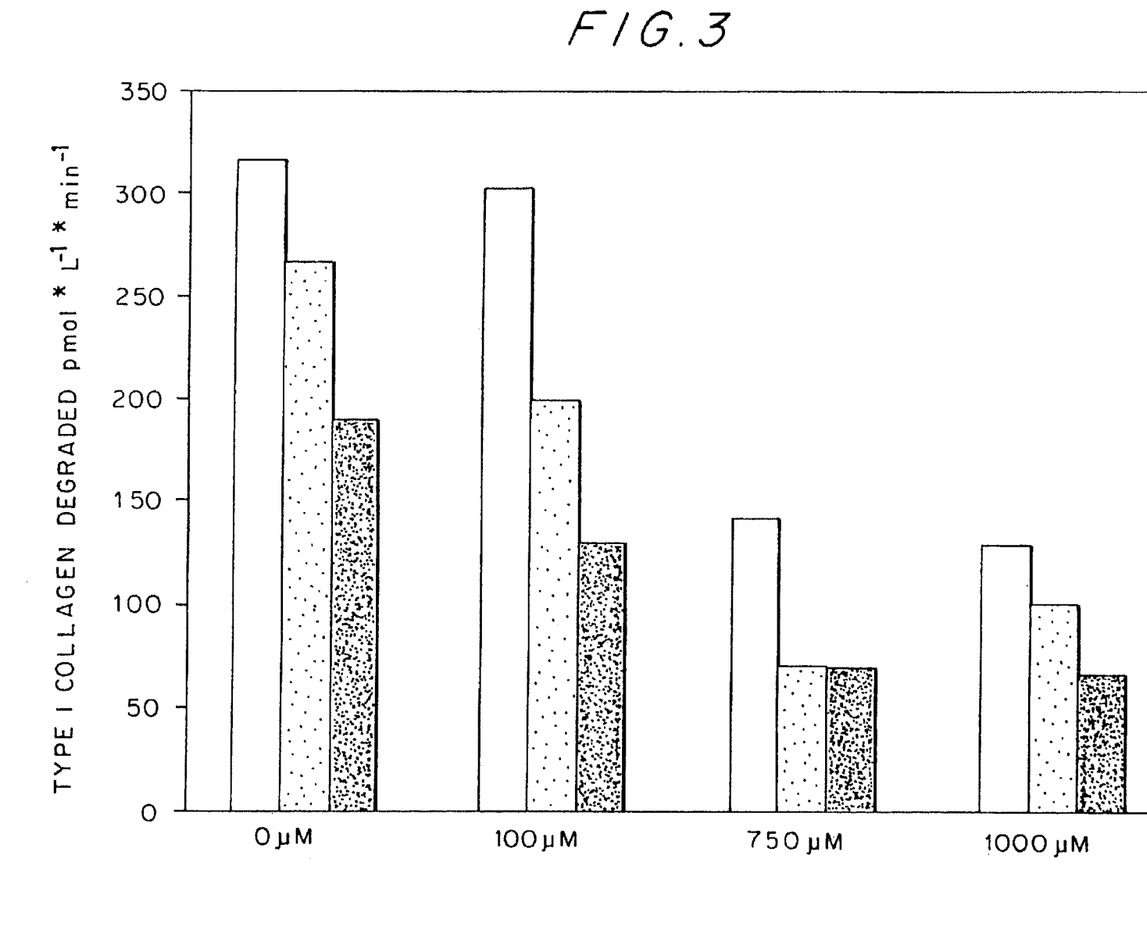
FIG. 3 is a block graph of the effects of clodronate on human neutrophil collagenase (MMP-8) activity.

FIG. 3 shows a diagram presenting the effect of clodronate on APMA-activated purified MMP-8. Three separate results of incubations are presented. The concentrations of clodronate are indicated.

EXAMPLE 4

Inhibition of Collagenase Activity in GCF from Periodontitis Patients by Clodronate Gingival crevicular fluid (GCF) from deep (>6 mm) periodontal pockets of patients with adult periodontitis has been shown by Western-blotting to contain autoactive MMP-8 (Sorsa et al., Ann. N.Y. Acad. Sci. 732:112–131, 1994) and was therefore used in this experiment. The samples were collected with filter strips placed gently on the opening of the gingival orifice approximately 1 mm into the sulcus for 2–5 minutes. The absorbed fluid was eluated with 75 µl per strip of 50 mM Tris-HCl, pH 7.5, containing 0.15 M NaCl and 1 mM $CaCl_2$. The samples were then centrifuged and aliquots of the supernatant were used for the enzyme assay. The GCF incubations with type I collagen and the effects of clodronate were performed using the same protocol as in Examples 1 and 2. The results of the five separate incubations are shown in FIG. 4.

Figure 4:
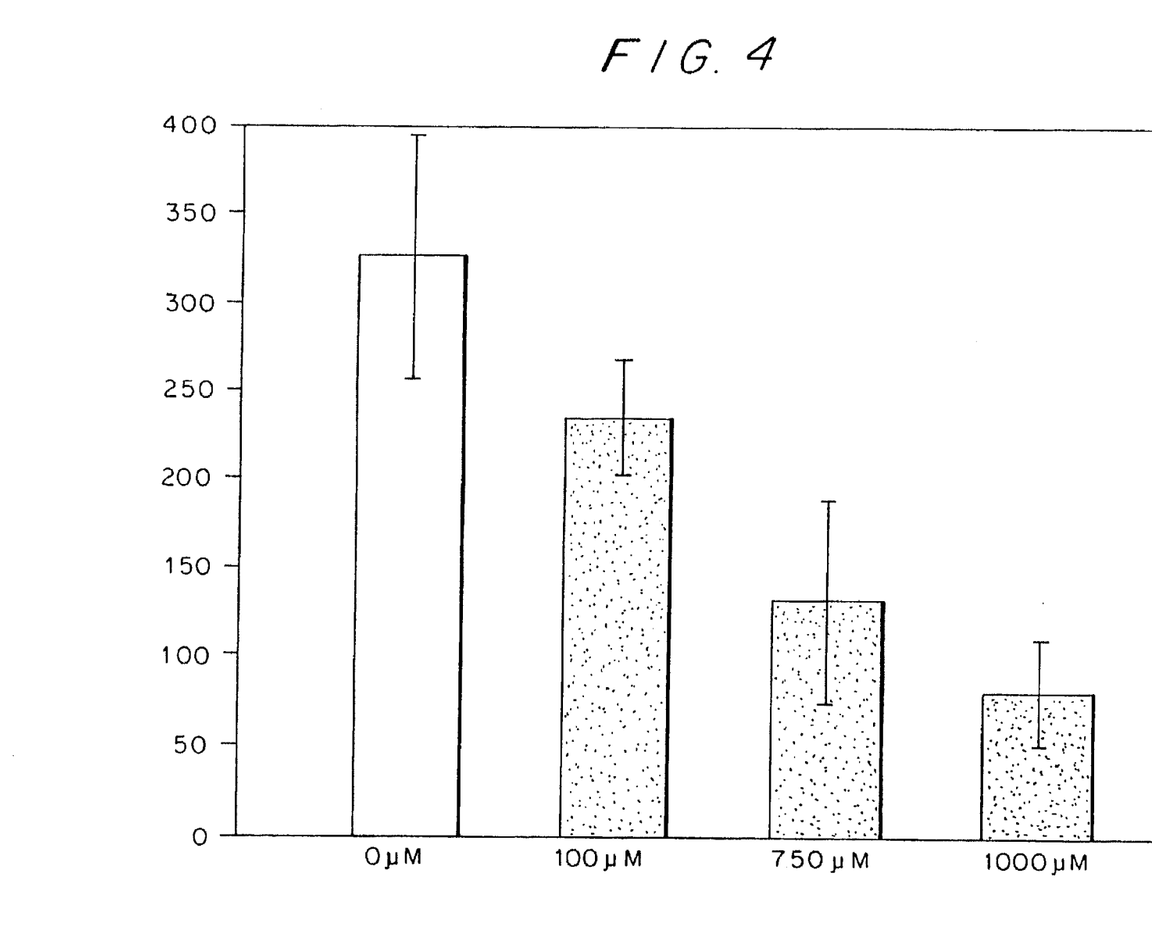
FIG. 4 is a block graph of the effects of clodronate on the collagenase activity in gingival crevicular fluid of human adult periodontitis patients.

FIG. 4 shows a diagram of the effect of clodronate on the autoactive collagenase activity of GCF. The columns present mean values with standard deviations of five incubations. The concentrations of clodronate are indicated.

EXAMPLE 5

Inhibition of Collagenase in Peri-implant Sulcular Fluid (PISF) from Peri-implant Patients by Clodronate Peri-implant sulcular fluid (PISF) from peri-implant pockets of loosening dental implants of five patients were used. The samples were collected with filter strips placed gently on the opening of the implant margin approximately 1 mm into the sulcus for 2 to 5 minutes. The absorbed fluid was eluated with 50 μl per strip of 50 mM Tris-HCl, pH 7.5, containing 0.15 M NaCl and 1 mm $CaCl_2$. The samples were then centrifuged and aliquots of the supernatant were used for the collagenase assay. The samples used in this experiment were also found to contain immunoreactive MMP-8 using specific polyclonal rabbit antiserum for human polymorphonuclear neutrophilic collagenase (MMP-8) by Western-blotting (Sorsa et al., Ann. N.Y. Acad. Sci. 732:112–131, 1994) as well as by functional characterization (Ingman et al., J. Clin. Periodontol. 21:26–31, 1994). The incubations with type I collagen and clodronate were performed using the same protocol as in Example 1 and 2. The results of five double incubations (n=10) are shown in FIG. 5.

Figure 5:
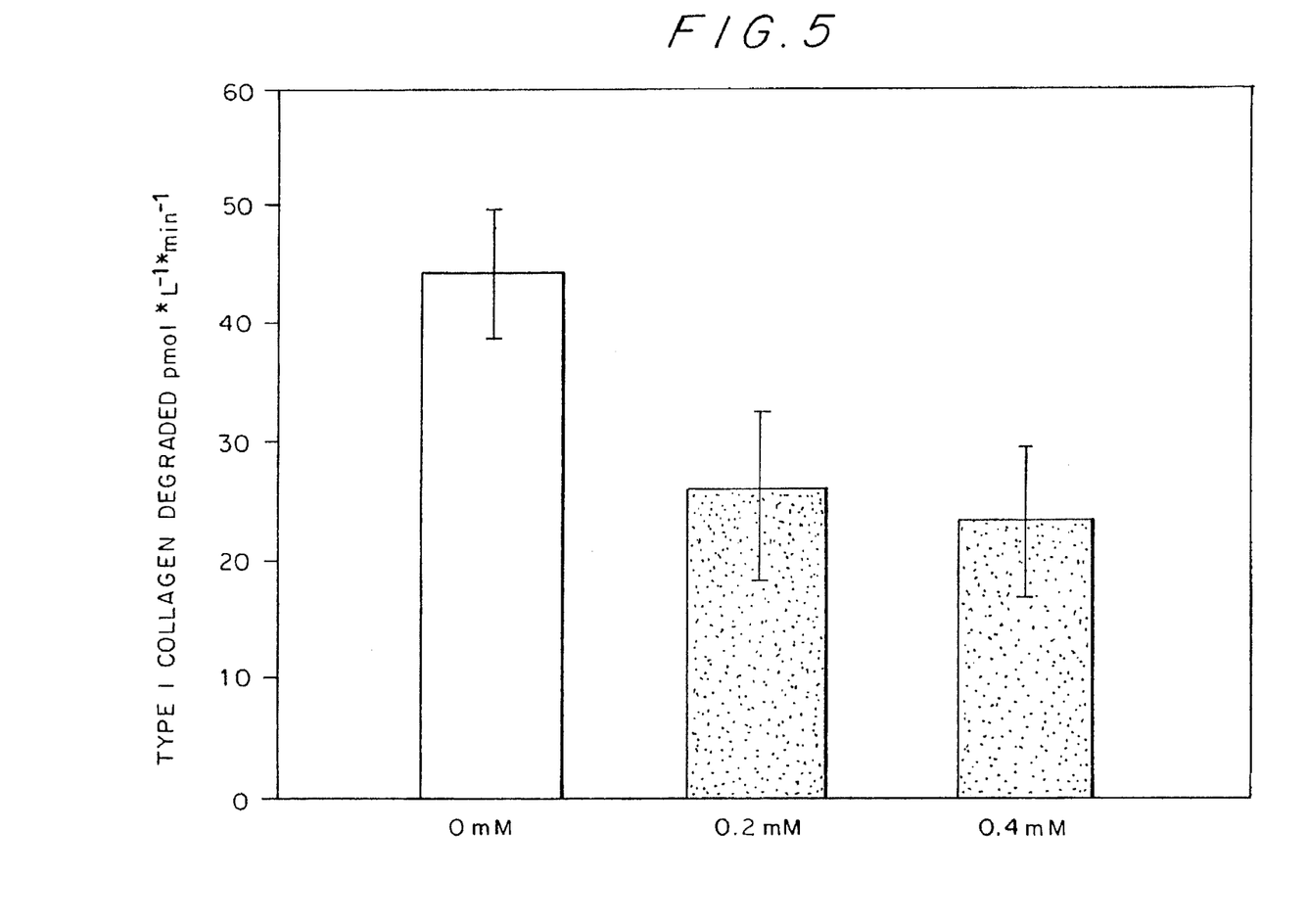
FIG. 5 is a block graph of the effects of clodronate on collagenase activity in the peri-implant sulcular fluid of peri-implant patients.

FIG. 5 shows a diagram of the effect of clodronate on PISF collagenase. The columns present mean values with standard deviations of ten separate incubations. The concentrations of clodronate are presented below each column.

As can be seen from the above Examples 1 to 5, the presence of bisphosphonates provides a significant inhibition/reduction of the activity of MMP-1 and MMP-8.

It should be noted that the values in the specific Examples 1 to 5 are relative and that they are not intended to indicate general absolute values for the inhibition rates. The obtained values are specific for the tests performed, and other absolute values may be obtained under different conditions. The Examples do, however, clearly indicate the inhibitive effect of bisphosphonates on the activity of MMPs. This inhibitive effect, as such, is not dependent on the test conditions.

PROPHETIC EXAMPLE 1

Treatment of Humans Suffering from Periodontitis

Gingival crevicular fluid (GCF) is taken from the periodontal pockets of an adult patient suffering from periodontitis. The GCF is shown to contain an elevated amount of MMP-8. Clodronate is administered orally to said patient for two weeks at a dosage of 2400 mg/day (capsules taken twice daily), whereafter the treatment is continued for two months at a dosage level of 1600 mg/day.

After the initial two weeks the enzyme activity in GCF has significantly decreased and after the whole treatment the enzyme activity is at a normal level indicating that the collagen degradation significantly decreases and the active tissue desecration associated with periodontitis also decreases.

The patient is monitored in subsequent inspections and the treatment is renewed at need.

PROPHETIC EXAMPLE 2

Treatment of Humans Suffering from Periodontitis

Gingival crevicular fluid (GCF) from the periodontal pockets of an adult patient is shown to contain a very high amount of MMP-8 indicating severe periodotitis. Etidronate is administered topically by a dentist to each afflicted tooth in a gel containing 1% etidronate. The treatment is repeated once or twice during five consecutive days.

The treatment results in a significant decrease of MMP-8 activities in the GCF of said patient. The treatment is repeated after three months at need.

PROPHETIC EXAMPLE 3

Treatment of Humans Suffering from Rheumatoid Arthritis

Arthritic synovial fluid is taken from the joints of an adult patient suffering from rheumatoid arthritis. The synovial fluid is shown to contain an elevated amount of MMP-1 indicating an active degradation of collagenase. Clodronate is administered as an infusion at a dosage of 4 mg/kg in saline solution for five consecutive days, whereafter the treatment is continued by oral administration of 2400 mg clodronate/day for two months.

After an initial two weeks the MMP-1 activity in the synovial fluid significantly decreases and after the whole treatment the enzyme activity is at a basically normal level indicating that the collagen degradation has stopped.

The patient is monitored in subsequent inspections and the treatment is renewed at need.

PROPHETIC EXAMPLE 4

Prophylaxis of Periodontitis in Humans Suffering from Diabetes Mellitus

A group of patients suffering from diabetes mellitus are monitored for periodontitis. Half of the group receive clodronate topically administered in a clodronate containing tooth paste used twice daily for several years. The other half of the group does not receive bis-phosphonate in any form.

The MMP-8 activity of the treated patients remains at a steady normal level. None of the patients prophylactically treated with clodronate develops periodontitis. Several of the patients in the untreated group develop periodontitis showing elevated levels of MMP-8 activity.

While there has been described what are presently believed to be the preferred embodiments of the present invention, those skilled in the art will realize that changes and modifications may be made thereto without departing from the spirit of the invention, and it is intended to claim all such changes and modifications as fall within the true scope of the invention.

It is especially envisaged that the matrix metalloproteinases will be found to play an important role in several diseases and disorders, in which their action has not so far been discovered. The invention is intended to encompass the use of bisphosphonates also in the treatment and prophylaxis of such conditions, as well as the formulation of bisphosphonates into various dosage forms for said treatment and prophylaxis.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A method of reducing of reducing a pathological excess of mammalian collagenolytic enzyme activity and an excessive degradation of connective tissue matrix protein components in a mammal in need thereof comprising:

administering to said mammal a bisphosphonate in an amount which is effective in reducing the matrix metalloproteinase (NMP) activity in said mammal.

2. The method of claim 1, which comprises administering to said mammal an effective amount of bisphosphonate which results in a significant reduction of the MMP dependent protein degradation in said mammal.

3. The method of claim 1, wherein said bisphosphonates comprises a bisphosphonate which is active as an inhibitor against at least one matrix metalloproteinase (MMP).

4. The method of claim 3, wherein said matrix metalloproteinase is selected from the group consisting of MMP-1, MMP-8 and a combination of MMP-1 and MMP-8, and wherein said mammal is a human having an increased level of MMP-1, MMP-8 or both MMP-1 and MMP-8.

5. The method of claim 1, wherein said bisphosponate is a geminal bisphosphonate having the general formula wherein R' and R" independently stand for a hydrogen or a halogen atom, a hydroxy, optionally substituted amino or optionally substituted thio group or an optionally substituted hydrocarbon residue.

6. The method of claim 5, wherein said bisphosphonate is selected from the group consisting of (1-hydroxyethylidene) bis-phosphonate, (dichloromethylene)bis-phosphonate (clodronate), (3-amino-1-hydroxypropylidene) bisphosphonate, (4-amino-1-hydroxybutylidene)bisphosphonate, {[4-chlorophenyl)thio]methylene}bisphosphonate, (6-amino-1-hydroxyhexylidene)bisphosphonate, [1-hydroxy-2-(3-pyridinyl)ethylidene]bisphosphonate, [3-(dimethylamino)-1-hydroxypropylidene] bis-phosphonate, [1-hydroxy-3-(methylpentylamino) propylidene]bis-phosphonate or a mixture thereof.

7. The method of claim 6, wherein said bisphosphonate is clodronate.

8. The method of claim 1, wherein said bisphosphonate is administered in a way selected from the group consisting of oral, intravenous, parenteral, subcutaneous and topical administration.

9. The method of claim 1 wherein said mammal is a human selected from a populace susceptible to an excess degradation of connective tissue matrix protein components selected from the group consisting of diabetics and health care workers, and wherein said bis-phosphonate is administered prophylactically.

10. The method of claim 1 wherein said mammal is a human, with the proviso that such human is not (a) a patient in need of a skeletal marker in the form of $^{99m}$technetium derivatives for diagnostic purposes in nuclear medicine, (b) a patient in need of administration of an anti-osteolytic agent, (c) a patient with ectopic calcification and ossification in need of an inhibitor of calcification, or (d) a patient in need of an anti-tartar agent.

11. The method according to claim 10 wherein said human is a patient selected from the group of patients in need of treatment of wounds, burns, fractures, lesions, ulcers, cancer and metastasis progression in connective tissues, rheumatoid arthritis and other arthitides, periodontitis, peri-implantitis, cysts, root canal treatment, AIDS, ulceration of the cornea, gastric ulceration, aftae, trauma, acne, psoriasis, loosening of end-osseal hip-protheses.

12. The method according to claim 1, wherein said excessive degradation of connective tissue matrix protein components in mammals comprises a physiological or pathological condition selected from the group consisting of wounds, burns, fractures, lesions, ulcers, cancer and metastasis progression in connective tissues, rheumatoid arthritis and other arthitides, periodontitis, peri-implantitis, cysts, root canal treatment, AIDS, ulceration of the cornea, gastric ulceration, aftae, trauma, acne, psoriasis, loosening of end-osseal hip-protheses.

13. The method according to claim 1, wherein said excessive degradation of connective tissue matrix protein components in mammals comprises periodontitis.

14. The method according to claim 1, wherein said excessive degradation of connective tissue matrix protein components in mammals comprises peri-implantitis.

15. The method according to claim 1, wherein said excessive degradation of connective tissue matrix protein components in mammals comprises cancer and metastasis progression in connective tissues.

16. A method of inhibiting extracellular activity of MMP-1, MMP-8 or both MMP-1 and MMP-8, in a mammal in need thereof comprising:

administering to said mammal a bisphosphonate in an amount which is effective in reducing the extracellular matrix MMP-1, MMP-8 or both MMP-1 and MMP-8 activity in said mammal.

17. A method according to claim 16 wherein said mammal is a human patient having an increased level of MMP-1, MMP-8 or both MMP-1 and MMP-8 and is in need of a treatment selected from the group consisting of treatments of wounds, burns, lesions, ulcers, rheumatoid arthritis or other arthritides, cysts, AIDS, ulceration of the cornea, gastric ulceration, aftae, trauma, acne and psoriasis.

* * * * *